(12) United States Patent
Metzinger et al.

(10) Patent No.: US 9,173,664 B2
(45) Date of Patent: Nov. 3, 2015

(54) INTRAMEDULLARY NAIL HOLDING DEVICE

(71) Applicant: Biomet Trauma, LLC, Warsaw, IN (US)

(72) Inventors: Anthony J. Metzinger, Winona Lake, IN (US); Paul Slagle, Leesburg, IN (US)

(73) Assignee: Biomet Trauma, LLC, Warsaw, IN (US)

( * ) Notice: Subject to any disclaimer, the term of this patent is extended or adjusted under 35 U.S.C. 154(b) by 241 days.

(21) Appl. No.: 13/796,138

(22) Filed: Mar. 12, 2013

(65) Prior Publication Data

US 2014/0276878 A1 Sep. 18, 2014

(51) Int. Cl.
*A61B 17/17* (2006.01)
*A45D 8/20* (2006.01)
*A61B 17/74* (2006.01)

(52) U.S. Cl.
CPC ......... *A61B 17/1725* (2013.01); *A61B 17/1721* (2013.01); *A45D 8/20* (2013.01); *A61B 17/744* (2013.01)

(58) Field of Classification Search
CPC ........... A61B 17/1721; A61B 17/1725; A61B 17/744; A45D 8/20
USPC ........ 606/62, 64, 96, 98; 269/254 R; 132/277
See application file for complete search history.

(56) References Cited

U.S. PATENT DOCUMENTS

| | | | |
|---|---|---|---|
| 2007/0131238 A1* | 6/2007 | Chudzik et al. | 132/277 |
| 2009/0032051 A1* | 2/2009 | Defenbaugh et al. | 132/277 |
| 2009/0272397 A1 | 11/2009 | Defenbaugh et al. | |
| 2012/0186602 A1 | 7/2012 | Hsu | |

* cited by examiner

*Primary Examiner* — Andrew Yang
(74) *Attorney, Agent, or Firm* — Schwegman Lundberg & Woessner, P.A.

(57) ABSTRACT

A targeting instrument system is provided and methods for positioning an internal fixation prosthesis, such as an intramedullary rod or nail, including a targeting guide device, an internal fixation prosthesis, and a detachable holding device. The holding device may include an exterior grip portion and a clamp portion defining an interior engaging surface for maintaining a locking alignment between the prosthesis and the targeting guide device during the placement of the internal fixation prosthesis into a subject. The holding device may be formed as a monolithic component including at least two flexible, spaced apart arms defining an elongated receiving channel extending from a proximal end configured to releasably engage the prosthesis and a distal end configured to releasably engage the targeting guide device. Alternatively, the holding device may include two pivotally coupled clamp bodies joined by a shaft rod.

18 Claims, 11 Drawing Sheets

INTRAMEDULLARY NAIL HOLDING DEVICE

INTRODUCTION

The present technology generally relates to surgical instruments and procedures, and more particularly, to targeting guide devices, their associated instrumentation, and procedures for the repair of fractured bones.

Hip fracture nail (HFN) systems, also broadly referred to as reconstruction nail systems, are available for surgically treating a wide range of proximal femoral fracture indications. HFN systems typically include an intramedullary nail sized and shaped for surgical implantation into a intramedullary canal of the fractured, proximal femur. The proximal portion of the nail has a smooth, transverse bore that retains a lag screw or the like having a distal end that anchors into the femoral head of the femur, such that the construct holds the femoral neck and the diaphysis (shaft) of the femur at a fixed angle with respect to each other, while allowing "sliding compression" of the fractured, proximal femur to promote proper healing. Typically this neck/shaft angle is in the range of about 125 to about 130 degrees. The proximal portion of the nail may also include another transverse, smooth bore that retains an anti-rotation screw alongside and proximal to the lag screw. Manufacturers typically provide HFN systems with both long and short versions of the nail and in various sizes to accommodate patient anatomy variations.

Surgeons usually implant the hip fracture nail and screws with the aid of an x-ray radio scope (fluoroscope) in order to verify proper reduction of the fracture and to properly position the nail and screws in the femur. It may be important to insert the distal end of the lag and anti-rotation screws into the central portion of the femoral neck and head so as not to weaken the construct or to break out through the articulation surface of the femoral head. Accordingly, manufacturers provide special instrumentation for implanting the HFN system. Such instrumentation typically includes a targeting guide device, or jig, that attaches to the end of the intramedullary nail.

The target jig, which may include the aid of radioscopic visualization, provides a handle for holding and positioning the nail into the femur. The target jig also includes target holes aligned with the lag screw and anti-rotation screw holes in the nail, to aid the surgeon in drilling the pilot holes into the femoral neck and head to receive the lag and anti-rotation screws. Portions of the target jig may be radiolucent in order to radioscopically visualize the nail, while other portions of the target jig may be radiopaque in order to provide visual references for aligning and positioning the nail inside the femur so that the axis of the lag screw passes approximately through the center of the femoral neck and head.

It is usually necessary for the surgeon to take several radioscopic images in the medial-lateral and anterior-posterior directions in order to reduce the fracture and to properly position the nail in the femur. This is primarily because it is often difficult for the surgeon to discern if the radioscopic view is optimal for directing a guide wire through the femoral neck and to the proper depth in the femoral head. The guide wire is needed for guiding a cannulated drill to create a pilot hole for the lag screw. Clearly, each radioscopic image increases exposure of the surgeon, staff, and patient to radiation and adds to the surgical procedure time and costs. What is needed, therefore, is improved instrumentation to aid the surgeon in properly implanting a hip fracture nail into the femur of a patient.

SUMMARY

This section provides a general summary of the disclosure, and is not a comprehensive disclosure of its full scope or all of its features.

The present teachings provide a detachable holding device for the temporary locking connection of an intramedullary implant to a targeting guide device. The holding device may include an exterior grip portion and a clamp portion. The clamp portion may define an interior engaging surface for coupling and maintaining a locking alignment between the intramedullary implant and the targeting guide device during the placement of the intramedullary implant into a subject. The holding device may be formed as a monolithic component including at least two flexible, spaced apart arms defining an elongated receiving channel.

The present teachings also provide a targeting instrument system for positioning an intramedullary implant. The system includes a targeting guide device, an intramedullary implant, a connecting bolt, and a detachable holding device. The detachable holding device includes an exterior grip portion and a clamp portion. The clamp portion defines an interior engaging surface that maintains a locking alignment between the intramedullary implant and the targeting guide device during the placement of the connecting bolt into the targeting guide device and the intramedullary implant.

The present teachings also disclose a method for establishing a temporary locking alignment between a targeting guide device and an intramedullary implant. The method includes coupling a proximal end of a detachable holding device to a connection end of the targeting guide device, and coupling a distal end of the detachable holding device to an intramedullary implant. The method further includes inserting a connecting bolt through a portion of the targeting guide device and fastening the connecting bolt to the intramedullary implant. The detachable holding device can be removed after the connecting bolt is secured within the intramedullary implant.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

It should be noted that the figures set forth herein are intended to exemplify the general characteristics of materials, methods, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DESCRIPTION OF VARIOUS EMBODIMENTS

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom.

Figure 1:
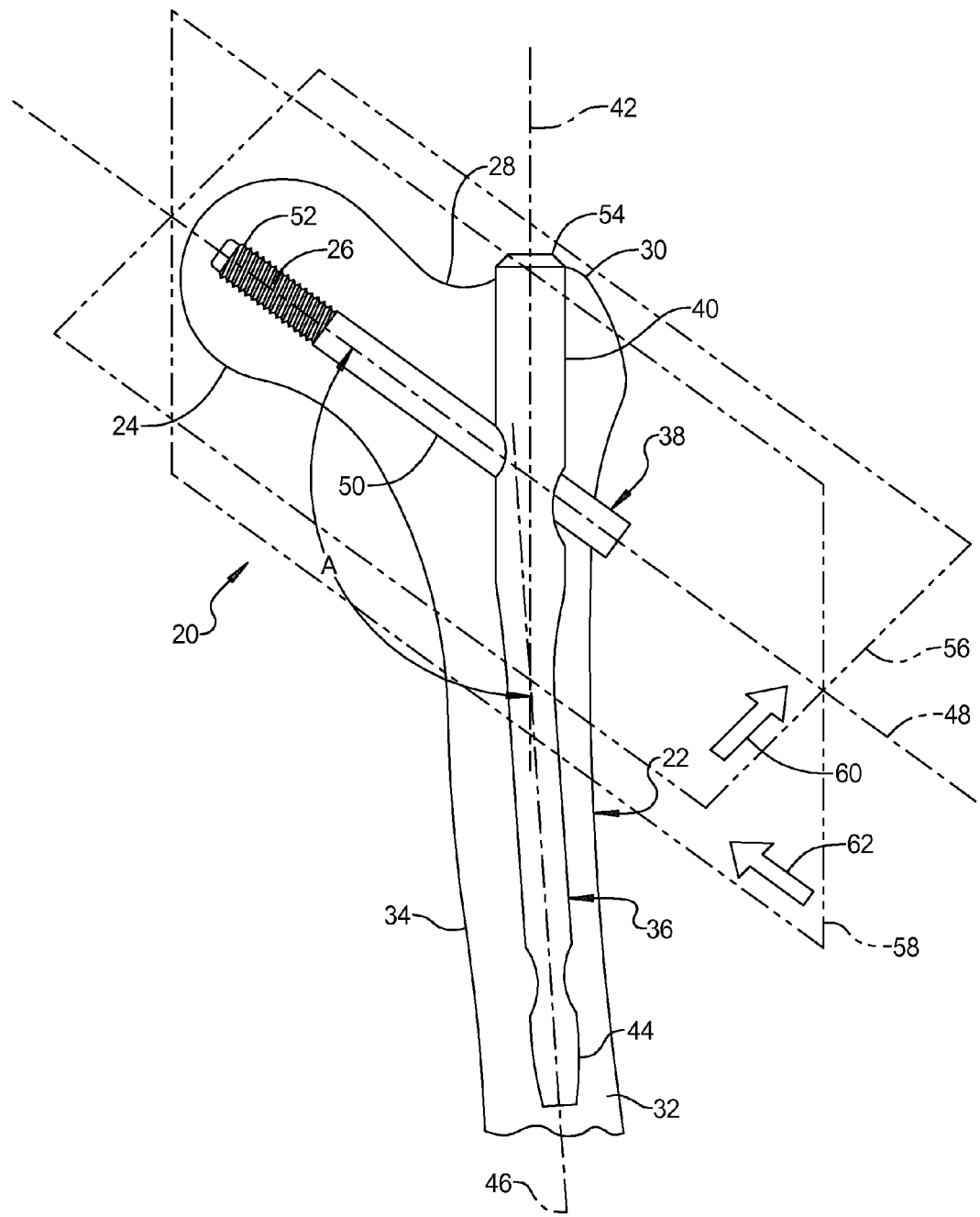
FIG. 1 is an anterior-posterior view of a hip fracture nail (HFN) prosthesis assembly, which includes an intramedullary (IM) nail and a lag screw defining a lag screw axis, implanted into a proximal femur of a subject according to various aspects of the present disclosure.

The present technology generally relates to instruments useful for the positioning of medical implant components and methods for improving the procedures for implanting medical devices and bone fracture repairs. As used herein, the term "implant" may be used to refer to an entire implant, or a portion thereof; portions may be as large or as small as necessary to accommodate the specific need. For example, an implant made in accordance with the present disclosure, generally including a nail and lag screw as shown in FIG. 1, may constitute the entire implant, or it may be used with one or more pieces or components that together form a final implant or implant assembly. The present disclosure encompasses a wide variety of therapeutic and cosmetic applications, for human and/or other animal subjects, and the specific materials, devices, and instruments used should be biomedically acceptable. As used herein, such a "biomedically acceptable" or "biocompatible" material or component is one that is suitable for use with humans and/or animals without undue adverse side effects (such as toxicity, irritation, and allergic response) commensurate with a reasonable benefit risk/ratio.

The terminology used herein is for the purpose of describing particular example embodiments only and is not intended to be limiting. In this disclosure, the terms "anterior," "posterior," "lateral," and "medial" generally refer to the front, back, outside, and midline of a surgical patient, respectively, although these terms are also used in reference to instruments and/or devices. It should also be noted that the term "user" may refer to a surgeon or any one of a number of individuals who assist the surgeon during a bone fracture repair procedure. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

FIG. 1 is an anterior-posterior view of a hip fracture nail prosthesis assembly 20 (or HFN prosthesis 20) implanted into a proximal portion of a femur 22 having a femoral head 24 with a center 26, a femoral neck 28, a greater trochanter 30, an intramedullary canal 32 and a femoral diaphysis 34. Shown as a basic assembly, the HFN prosthesis 20 includes at least an intramedullary nail 36 (or IM nail 36) and a lag screw 38. The IM nail 36 includes a proximal shaft portion 40 defining a proximal shaft axis 42 and a distal shaft portion 44 defining a distal shaft axis 46 that may be slightly inclined relative to proximal shaft axis 42 to conform to the shape of femur 22. The lag screw 38 defines a lag screw axis 48 and includes a proximal barrel portion 50 and a distal threaded portion 52. A transverse bore in the proximal portion 40 of the IM nail 36 slidingly retains the barrel portion 50 of the lag screw 38. The lag screw axis 48 and distal shaft portion axis 46 define a femoral neck-diaphysis angle indicated by the letter A, which corresponds approximately to the angle formed between the femoral neck 28 and the femur diaphysis 34. For most patients, this angle can approximately be in the range of about 125-135 degrees.

The distal threaded portion 52 of the lag screw 38 is designed for threadable engagement into the bone in the center 26 of the femoral head 24. However, it should be noted that there are different, but functionally equivalent, devices for anchoring into the femoral neck 28 and femoral head 24, including "blade" types of lagging devices for use with femoral nails, and reference to the distal threaded portion 52 of the lag screw 38 is not intended to be limiting.

The HFN prosthesis 20 may optionally include an end cap 54 and a retaining screw (hidden) inside of the internally threaded, proximal portion 40 of the IM nail 36 for retaining the lag screw 38. All of the components of the HFN prosthesis 20 may be formed from any one or more of a number of biocompatible, radiopaque materials, including a titanium alloy and stainless steel, as is well known in the art.

FIG. 1 also shows a first plane 56 that is orthogonal to a second plane 58. The intersection of the first plane 56 and the second plane 58 coincides with the lag screw axis 48. A first line of sight 60 is contained in the first plane 56. A second line of sight 62 is contained in the second plane 58. The first line of sight 60 and the second line of sight 62 may generally correspond to the optimal set-up directions of a radioscopic imaging device when positioning the IM nail 36 in the femur 22 in order to direct a targeting guide wire along the lag screw axis 48 and through the center 26 of the femoral head 24. Once properly inserted into femoral neck 28 and femoral head 24, a targeting guide wire may be used to safely guide a cannulated drill to create a pilot hole for the lag screw 38, as is well known in the art.

The actual direction of the first line of sight 60 within the first plane 56 with respect to the lag screw axis 48 may vary depending on the skill level of the user. Optimally, however, the first line of sight 60 is approximately perpendicular to the lag screw axis 48 and within the first plane 56. This may be especially significant when inserting a guide wire into the femoral head 24 to the desired depth to prevent penetration of the guide wire tip through the articulation surface of the femoral head 24. Similarly, the actual direction of the second line of sight 62 within the second plane 58 with respect to the distal shaft axis 46 may vary, depending again on the skill level of the user. As shown, the optimal direction of the first line of sight 60 is approximately parallel to the lag screw axis 48 and within the second plane 58. As will be described, particular features of the devices disclosed herein may assist the user in radioscopically visualizing the IM nail 36 along the first and second lines of sight 60, 62 in order to properly set the insertion depth and the version angle of the IM nail 36 in the femur 22.

The HFN prosthesis 20 may also include an anti-rotation screw (not shown) as noted previously. The present disclosure, however, is directed primarily to devices and procedures associated with the proper positioning of the IM nail 36 and the lag screw 38 into the femur 22, since the positioning of the anti-rotation screw into the femur 22 is predetermined by the prior positioning of the lag screw 38 into the femur 22. The HFN prosthesis 20 may also include additional screws and other internal components not described herein. Additional description of an exemplary device that is generally similar to the HFN prosthesis 20 and that includes an anti-rotation screw may be found in U.S. Pat. App. No. 2006/0106386 entitled "Orthopedic Screw and Method" filed by E. Reber, et al., on Jun. 28, 2005, incorporated by reference in its entirety.

Figure 2:
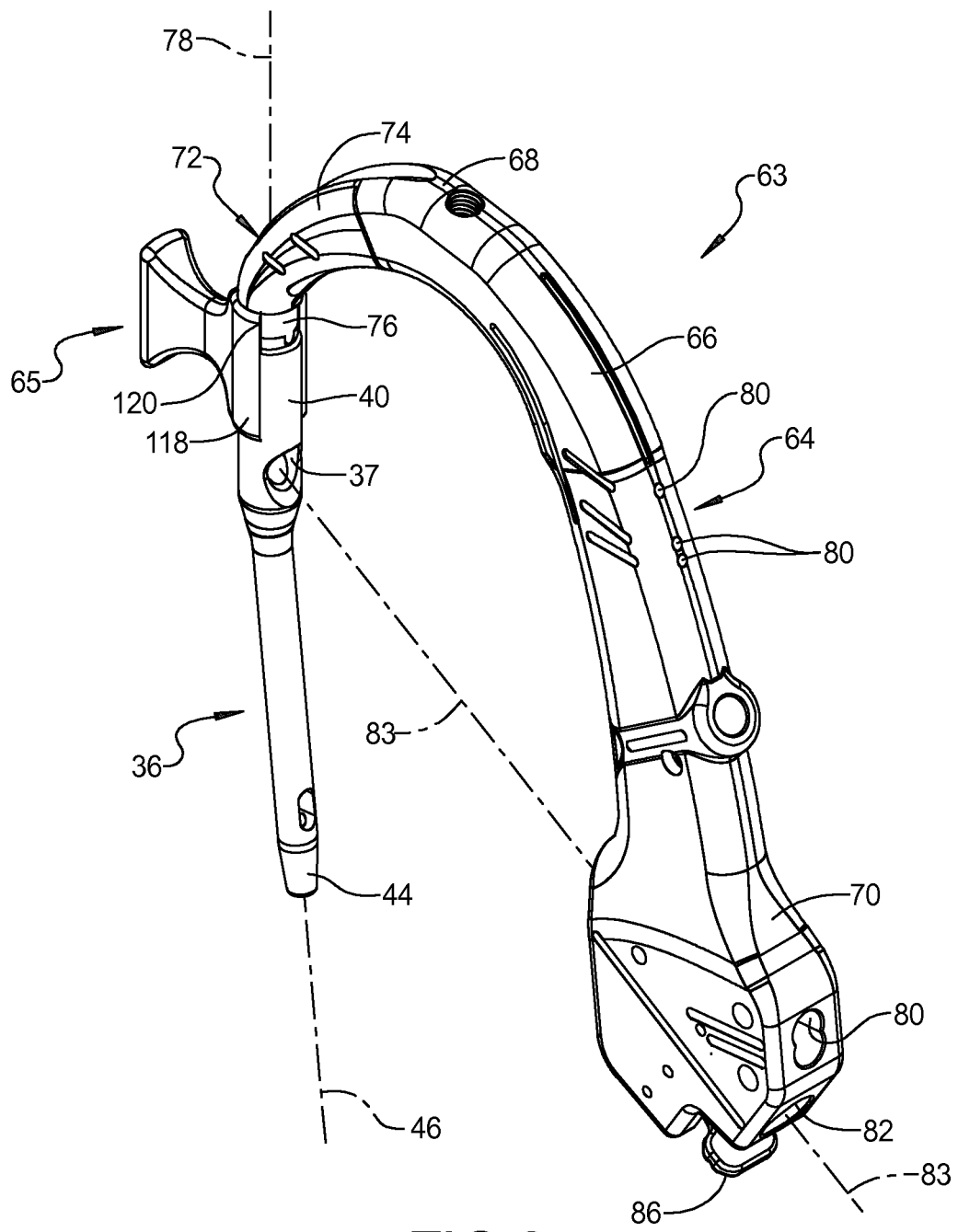
FIG. 2 is a perspective view of a targeting instrument system according to various aspects of the present teachings, shown with a targeting guide device in temporary locking alignment with the IM nail of FIG. 1 via a detachable holding device.
Figure 14:
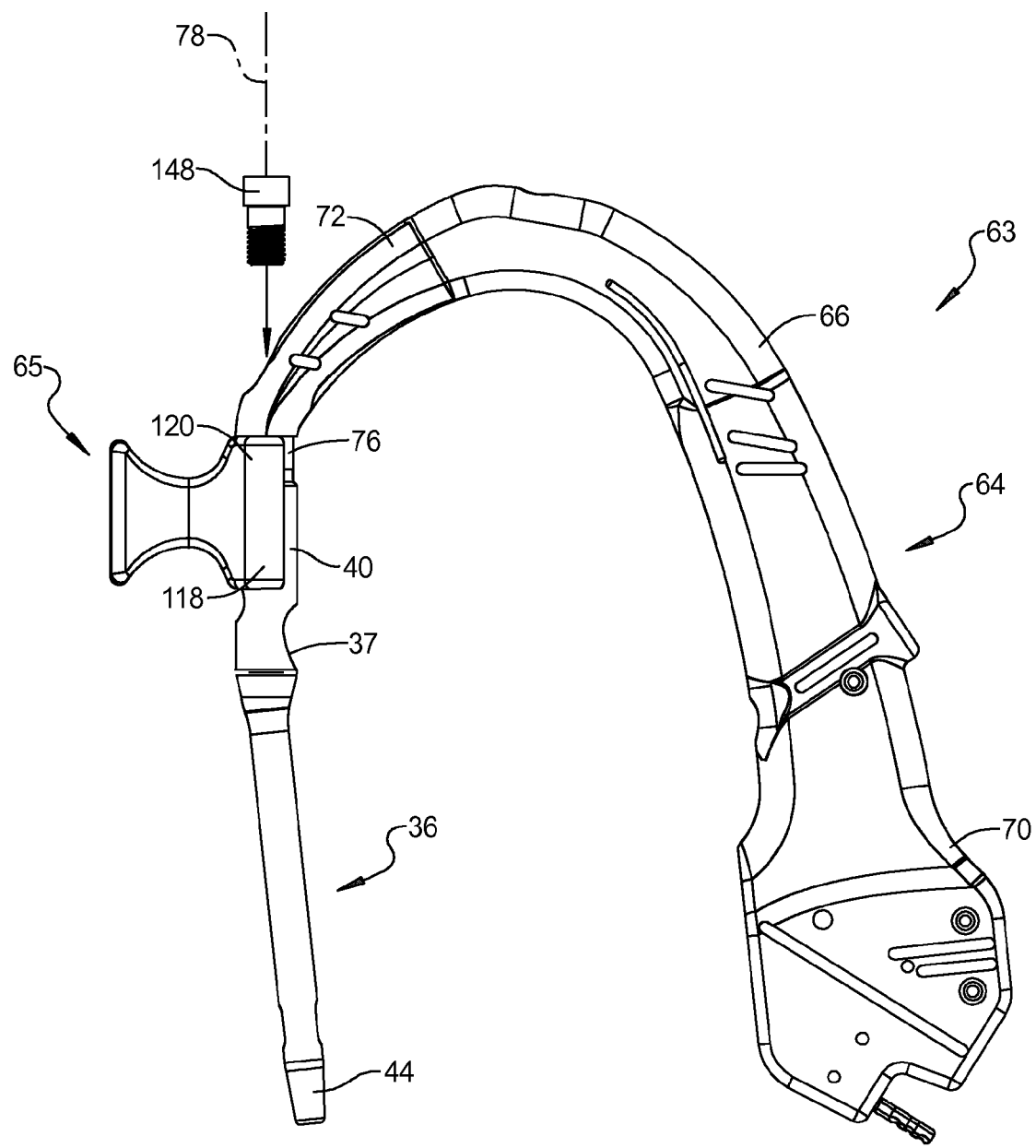
FIG. 14 is side plan view of the targeting instrument system of FIG. 2 with the detachable holding device coupled to the IM nail and the connection end of the targeting guide device.

FIG. 2 is a perspective view of a targeting instrument system 63 including a targeting guide device 64 (or target jig 64) shown in connecting alignment with the IM nail 36 using a detachable holding device 65. As will be described in detail, the detachable holding device 65 releasably couples to the targeting guide device 64 and the IM nail 36 to aid the user in maintaining alignment of the targeting guide device 64 and the IM nail 36 while inserting a connecting bolt 148 (FIG. 14). The targeting guide device 64 may be substantially U-shaped and include an arcuate-shaped handle 66 having a superior end 68 and an inferior end 70. The handle 66 may be formed from a radio-translucent, biocompatible material such as carbon-filled PEEK. A nose component 72 connects to the superior end 68 of the handle 66. The nose component 72 includes a yoke portion 74 and a shaft portion 76 with a connection end 96 (FIG. 5) that extends distally from the superior end 68 of the handle 66 to define a nose component axis 78. The nose component axis 78 is coaxial with the proximal shaft axis 42 (FIG. 1) of the IM nail 36 when the IM nail 36 is attached to the targeting guide device 64. The nose component 72 may be formed from a biocompatible, radiopaque material such as a titanium alloy or a stainless steel.

As shown in FIG. 2, the handle 66 of the targeting guide device 64 may include a plurality of wire holes 80 defining various respective target axes (not shown). The inferior end 70 of the handle 66 includes a lag screw target hole 82 defining a lag screw target axis 83. When the IM nail 36 is coupled to the targeting guide device 64, the lag screw hole 37 of the IM nail 36 is aligned with the lag screw target axis 83. A clamp element 86 assembles to the inferior end 70 of the handle 66. A user may attach the targeting guide device 64 to the IM nail 36 and manipulate the IM nail 36 into the femur 22 such that the lag screw target axis 83 passes approximately through the center 26 of the femoral head 24 prior to drilling a pilot hole for the lag screw 38.

Figure 3:
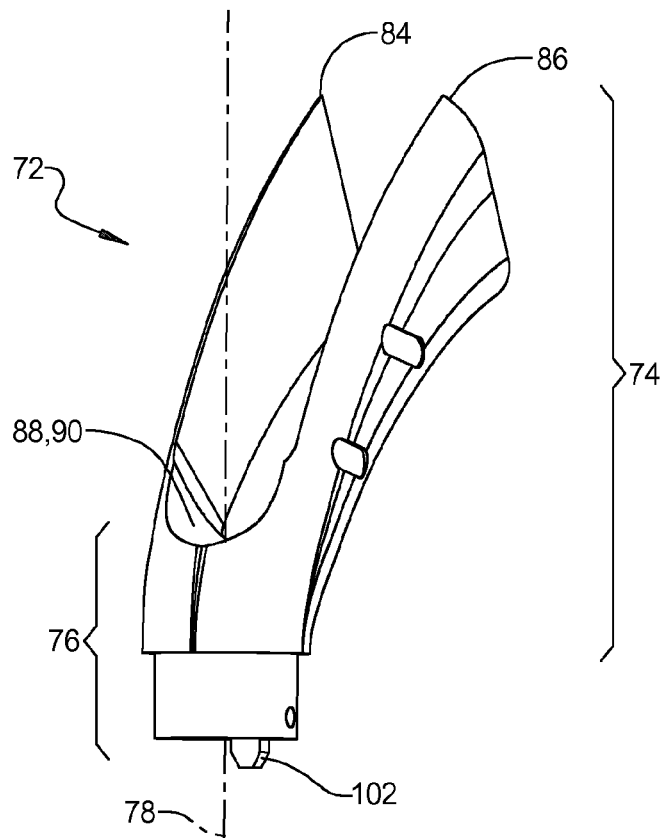
FIG. 3 is a detailed, perspective view of the nose component of the targeting guide device of FIG. 2.
Figure 4:
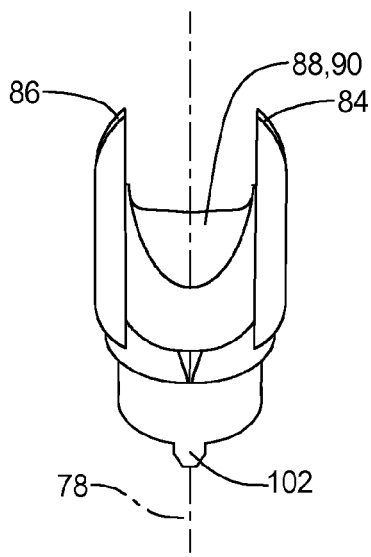
FIG. 4 is a front view of the nose component of FIG. 3.

FIG. 3 is a detailed, perspective view and FIG. 4 is a front view (corresponding to the medial-lateral view when targeting guide device 64 is used to position the IM nail 36 in femur 22) of the nose component 72, showing a yoke portion 74 and a shaft portion 76. The yoke portion 74 has a first arm 84 and an opposing second arm 86, together forming an alignment sight 88 defining a U-shaped gap 90 that centers on the shaft portion axis when viewed as shown in FIG. 4. When the nose component 72 is preferably formed from a radiopaque material, the alignment sight 88 will be visible on a radioscopic image. The targeting guide device 64 may be adapted for single use disposability or for repeated sterilizations using conventional techniques to allow usage for multiple surgical procedures.

Figure 5:
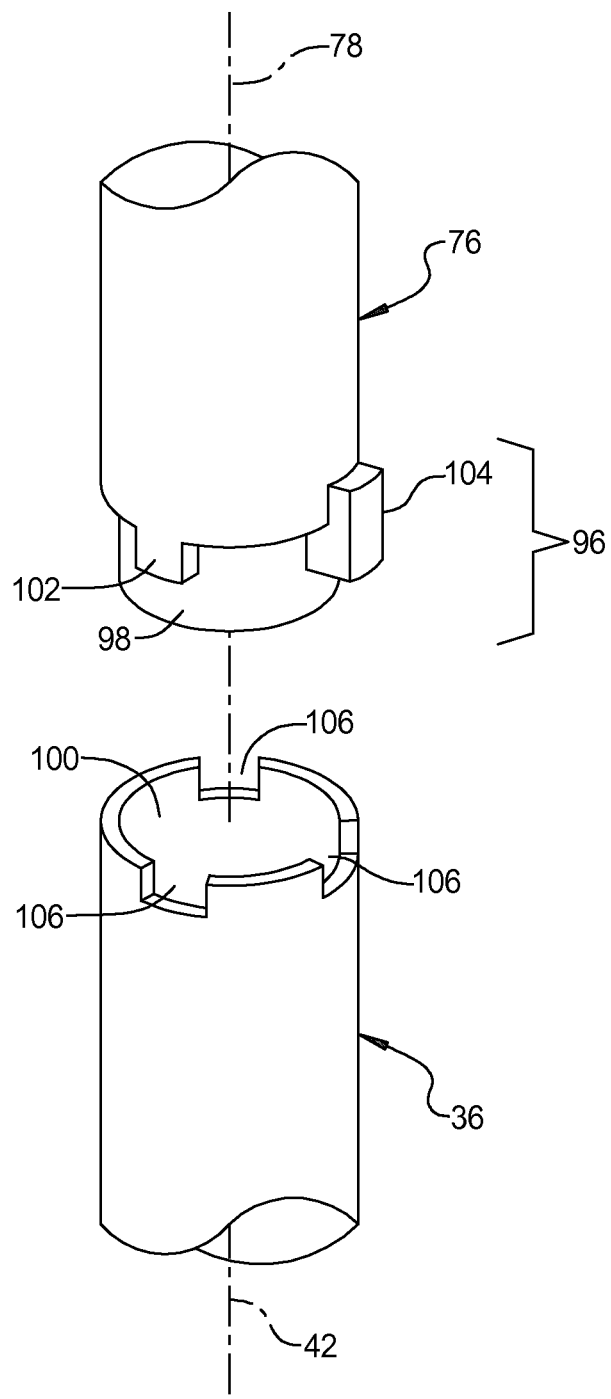
FIG. 5 is a detailed perspective view of the shaft of the nose component in connecting alignment with the IM nail.

FIG. 5 illustrates a detailed perspective view showing one aspect of the shaft 76 of the nose component 72 in connecting alignment with the IM nail 36. In various aspects, the nose component 72 of the targeting guide device 64 and the IM nail 36 include respective interlocking features preventing rotation of the IM nail 36 with respect to the targeting guide device 64. As shown, the connection end 96 may include a plurality of radially spaced apart flutes 102, 104. At least one of the flutes 104 may radially extend out a distance perpendicular to the shaft 76, configured for alignment with the detachable holding device 65, as will be discussed below. The IM nail 36 may include a plurality of recesses 106 having appropriate widths to receive the flutes 102, 104. An optional recessed region 98 may be defined at the connection end 96 of the shaft 76 for a press-fit or friction-fit connection with a commensurate bore or recess defined in the IM nail 36.

Figure 6:
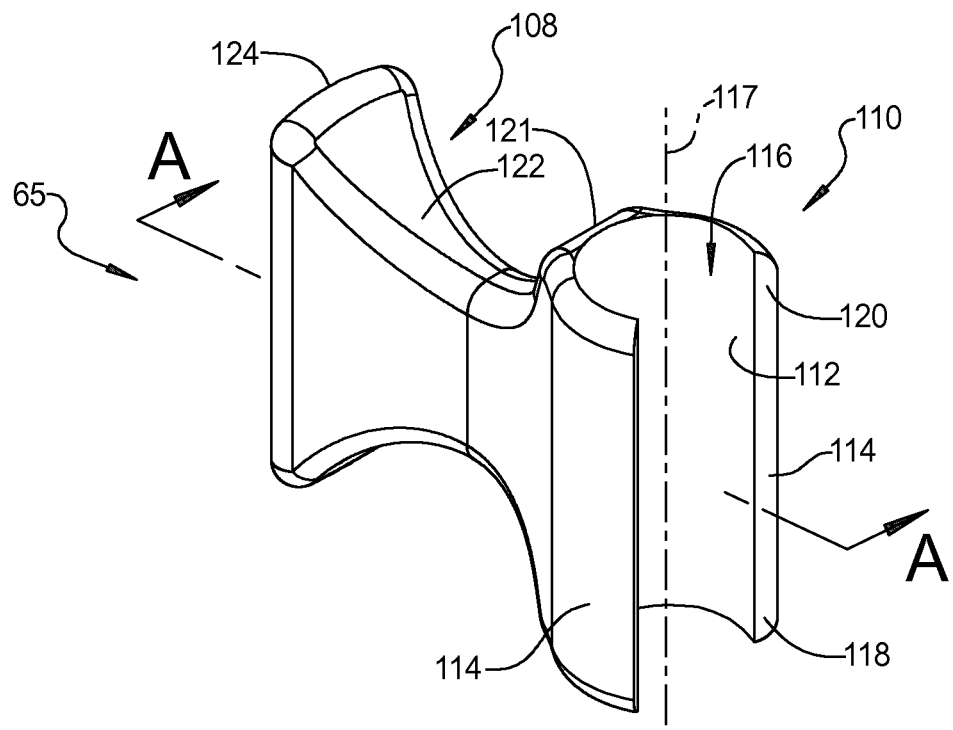
FIG. 6 is a first perspective view of an exemplary detachable holding device according to the present disclosure.
Figure 7:
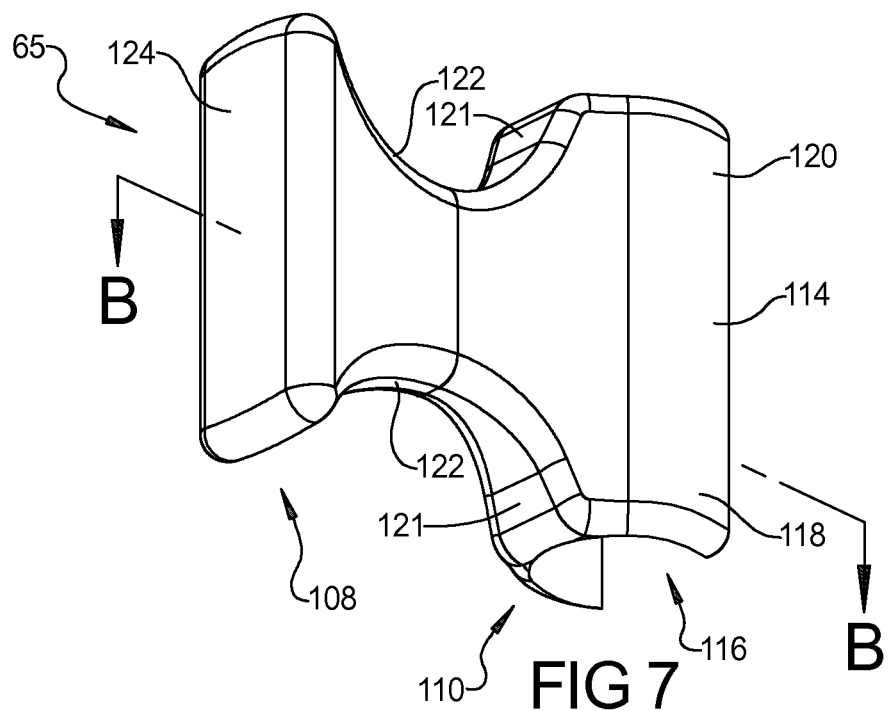
FIG. 7 is a second perspective view of the detachable holding device of FIG. 6.
Figure 8:
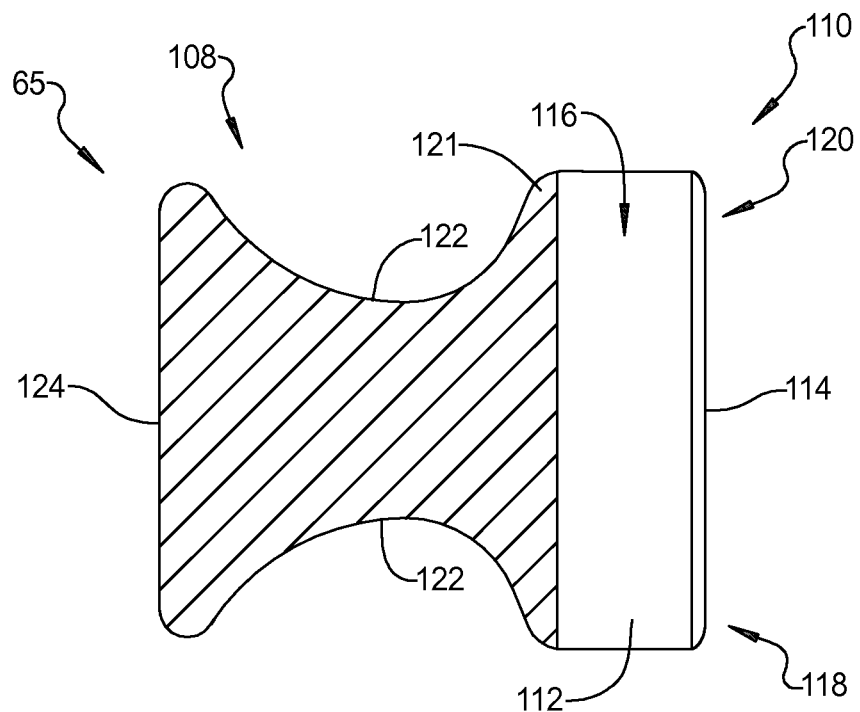
FIG. 8 is a cross-sectional view of the detachable holding device of FIG. 6 taken along the line A-A.
Figure 9:
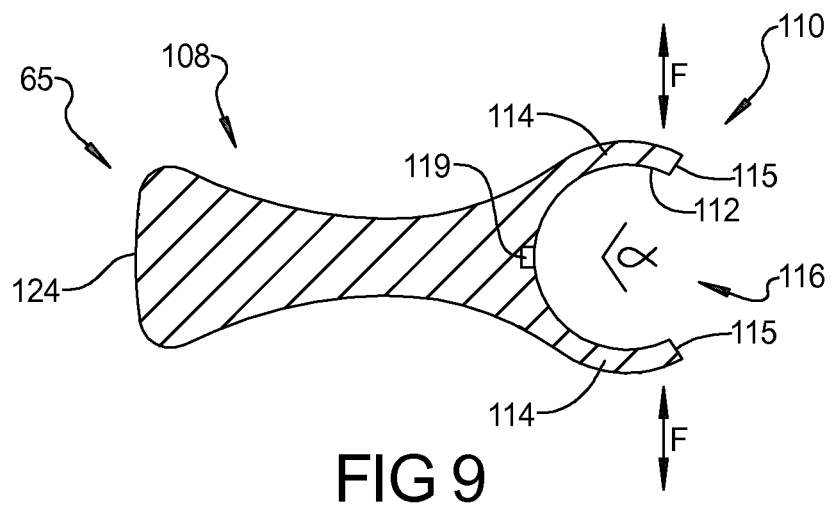
FIG. 9 is a cross-sectional view of the detachable holding device of FIG. 7 taken along the line B-B.

FIGS. 6 and 7 illustrate perspective views of one exemplary detachable holding device 65 according to various aspects of the disclosure. FIGS. 8 and 9 are cross-sectional views of the detachable holding device taken along the lines A-A and B-B of FIGS. 6 and 7, respectively. As shown, the detachable holding device 65 may include an exterior grip portion 108 and a clamp portion 110. The clamp portion 110 may define an interior engaging surface 112 configured for coupling and maintaining a temporary locking alignment and connection between the IM nail 36 and the targeting guide device 64 when inserting the connecting bolt 148.

In various aspects, the detachable holding device 65 can be formed as a monolithic component. For example, the holding device 65 can comprise a biocompatible polymeric material formed using injection molding techniques as are known in the art. In other aspects, the holding device 65 may be a machined polymer. In still other aspects, the holding device 65 may comprise more than one component fastened together. The holding device 65 can be made of various biocompatible polymers, resins, and plastics having a degree of flexibility sufficient to grippingly engage the targeting guide device 64 and the IM nail 36. Non-limiting examples include polyester based polymers, polyether ether ketone (PEEK), and polyphenylsulfones such as RADEL® resins (commercially available from Solvay Advanced Polymers in Alpharetta, Ga.). Because the holding device 65 is not a permanent part of the implant, and not meant to remain in the subject after the implant procedure, it may comprise one or more radiopaque markers visible in x-rays. In other aspects, the holding device 65 may include a base material, such as a biocompatible metal or ceramic, that is subsequently covered or coated with a polymer or resin. Still further, the interior engaging surface 112 may be roughened or coated to assist with the gripping connection.

As best shown in FIGS. 6 and 9, the clamp portion 110 may include two flexible, spaced apart arms 114 defining an elongated receiving channel 116 having a substantially C-shaped cross-section. The spaced apart arms 114 may be joined at a base area 121 and configured to flex or move in the F directions as shown in FIG. 9. In various aspects, the angle α formed between the edges 115 of the arms 114 may be between about 90 and about 150 degrees, for example about 120 degrees. In certain aspects, the arms may be temporarily flexed apart to permit a snap-fit coupling to the targeting guide device 64 and/or the IM nail 36. As shown, the elongated receiving channel 116 extends along a longitudinal axis 117 from a distal end 118 configured to releasably engage and couple the IM nail 36 to a proximal end 120 configured to releasably engage and couple the connection end 96 of the targeting guide device 64. With specific reference to FIG. 9, the elongated receiving channel 116 may define one or more interlocking features such as a longitudinally extending recess 119 or protrusion (not shown) configured to cooperate with one or more of the flutes 102, 104 of the connection end 96 of the targeting guide device 64 or recesses 106 in the IM nail 36. For example, the radially extending flute 104 of FIG. 5 can be aligned and engaged with the longitudinal extending recess 119 of the holding device 65 as depicted in FIG. 9. In this regard, the holding device 65 is prevented from rotating with respect to the targeting guide device 64. At the same time, the radially extending flute 104 (and/or a longitudinally extending flute 102) can be aligned with a respective recess 106 of the IM nail 36, such that the targeting guide device 64 is prevented from rotating with respect to the IM nail 36. It should be understood that the specific design, configuration and number of flutes, recesses, notches, protrusions, and the like can be varied as known in the art such that they effectively lock the spatial orientation, alignment, and relative movement between the targeting guide device 64, IM nail 36, and/or the holding device 65.

The exterior grip portion 108 may have various shapes, sizes, and configurations formed in an ergonomic manner such that the holding device 65 can be positioned and moved in an easy and convenient manner in order to be placed in a temporary locking connection with the targeting guide device 64 and IM nail 36. As shown, the exterior grip portion 108 extends a distance in a direction substantially perpendicular to the longitudinal axis and defines recessed or curved areas 122 extending from the base area 121 to a distal end 124, suitable for gripping by the user with a finger and thumb. It should be understood that the specific shape and size of the exterior grip portion 108, as well as the connecting relationship and angular position relative to the clamp portion, can be configured as desired for the intended purpose. In certain aspects, the exterior grip portion 108 may simply be defined as the exterior of the clamp portion 110.

Figure 10:
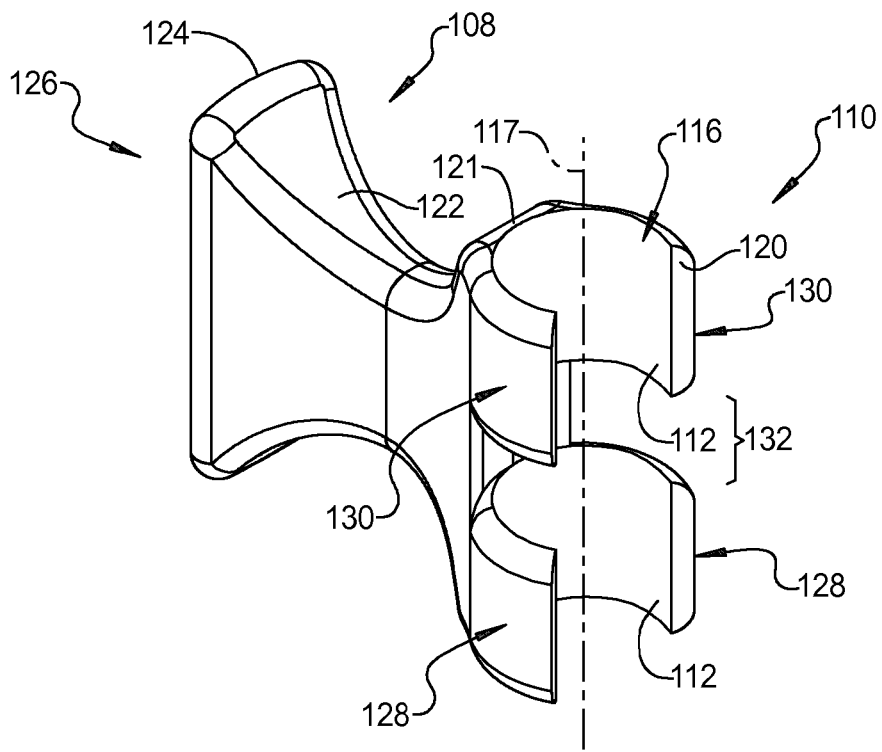
FIG. 10 is a perspective view of another exemplary detachable holding device.

FIG. 10 illustrates a perspective view of another exemplary detachable holding device 126 similar to FIGS. 6 and 7, but with plurality of flexible arms. The holding device of FIG. 10 includes a distal pair of arms 128 configured to releasably engage the IM nail 36 and a proximal pair of arms 130 configured to releasably engage the targeting guide device 64. Each pair of arms 128, 130 may be of similar size, shape, and configuration (as shown) separated from one another by a small gap region 132. It is also envisioned that the pairs of arms 128, 130 may alternatively each define a receiving channel having a different configuration. By way of example, one of the pairs of arms 128, 130 may define a receiving channel having a diameter greater than the other.

Figure 11A:
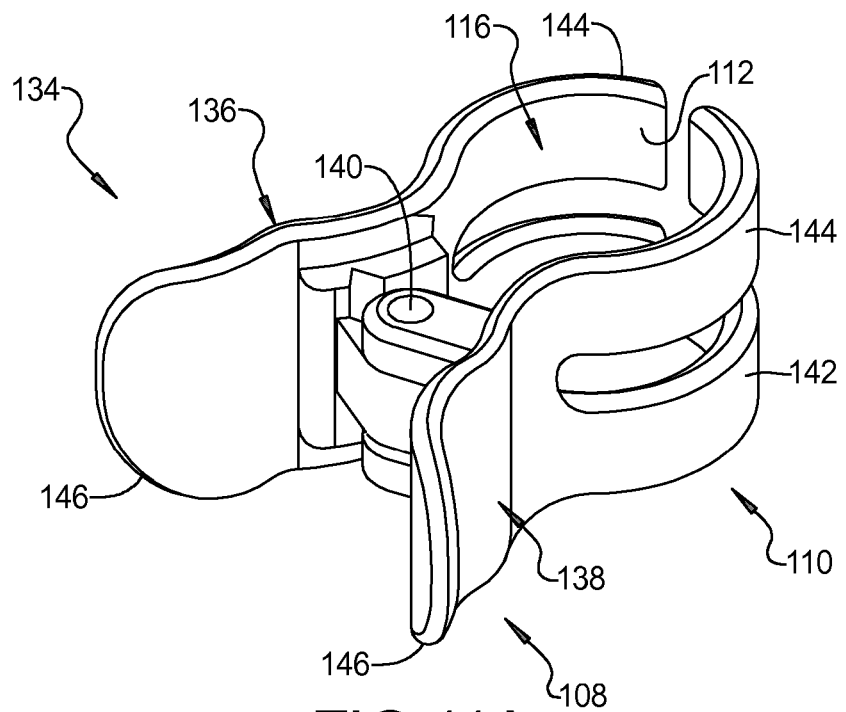
FIG. 11A is a perspective view of yet another exemplary detachable holding device having two biased clamp portions joined by a shaft rod.

FIG. 11A is a perspective view of yet another exemplary detachable holding device 134 having two biased clamp portions 136, 138 joined by a shaft rod 140. The clamp portions 136, 138 may be substantially identical to one another or have different configurations, biased in a closed position with a biasing member such as a torsion spring (not shown) as is well known in the art. Although shown with a distal pair of arms 142 and a proximal pair of arms 144, the holding device may be provided with just two arms, similar to FIG. 6, with both aspects defining an elongated receiving channel 116. Because the clamp portions 136, 138 are movable and separable from one another by grasping and pressing the ends 146 of the exterior grip portion 108 together, the arms 142, 144 may not need to be flexible, or have the same degree of flexibility as in other aspects. In addition to biocompatible polymeric materials, the clamp portions 136, 138 may also be formed of a biocompatible metal or metal alloy, and the biasing member may be provided with the ability to exert an increased biasing force for a stronger temporary locking connection than that provided in other aspects. In various aspects, the interior engaging surface 112 of the arms 142, 144 may be curved or contoured such that they are configured to define a variably shaped elongated receiving channel 116 commensurate with a diameter of the IM nail 36 and/or the connection end 96 of the targeting guide device 64. For example, the interior engaging surface 112 may be provided with a variable radius of curvature configured to grippingly engage a variety of different diameters. In this regard, it is envisioned the holding device 134 may accommodate existing IM nails 36 and targeting guide devices 64 having non-standard diameters or shapes.

Figure 11B:
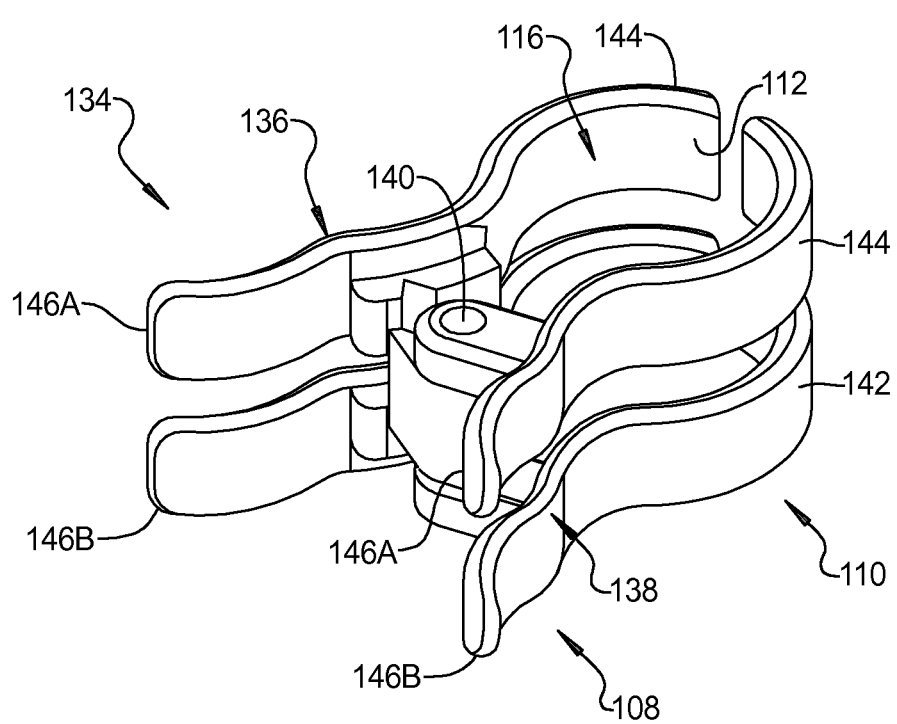
FIG. 11B is a perspective view of still another exemplary detachable holding device having two pairs of biased clamp portions operated independently from one another.

FIG. 11B is a perspective view of still another exemplary detachable holding device 134 having two pairs of biased clamp portions 136, 138 operated independently from one another. As shown, the distal pair of arms 142 is opened by grasping a first set of ends 146B, while the proximal pair of arms 144 is independently opened by grasping a second set of ends 146A. The configuration of the holding device 134, including the number of shaft rods 140 and biasing members (not shown), may vary as desired. As such, the particular designs shown in FIGS. 11A and 11B are not intended to be limiting in any regard. As non-limiting examples, the pairs of arms 142, 144 may have the same or different shape, the interior engaging surface 112 may be provided with the same or different contours or profiles, and biasing members may be provided with different forces.

Additional specific descriptions of other instrument components in relation to hip fracture nail systems can also be found in U.S. Pat. No. 8,257,354 and pending application Ser. No. 13/633,913 (published on Jan. 31, 2013 as U.S. Pub. No. 2013/0030444), the entire specifications of which are incorporated herein by reference.

Figure 12:
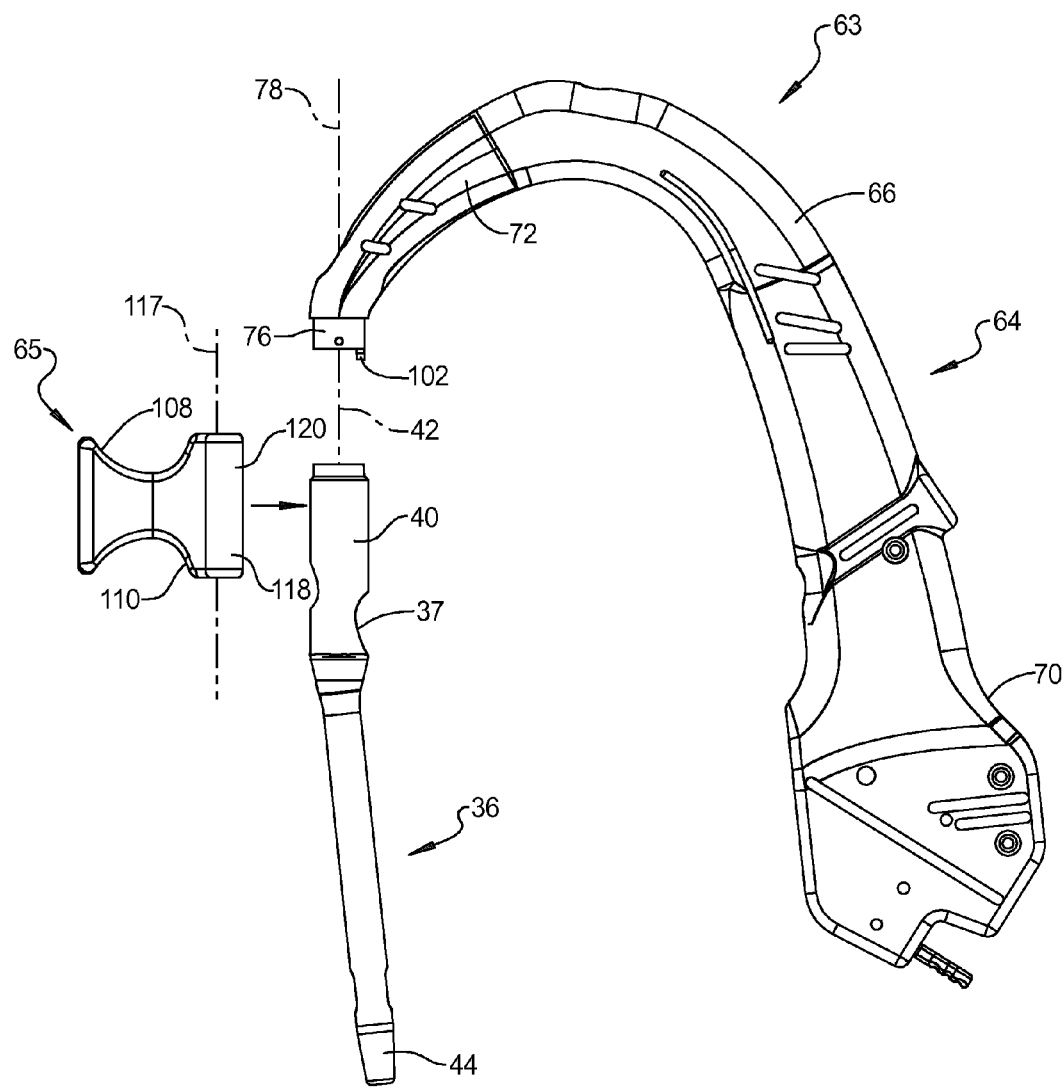
FIG. 12 is an exploded side plan view of the targeting instrument system of FIG. 2.
Figure 13:
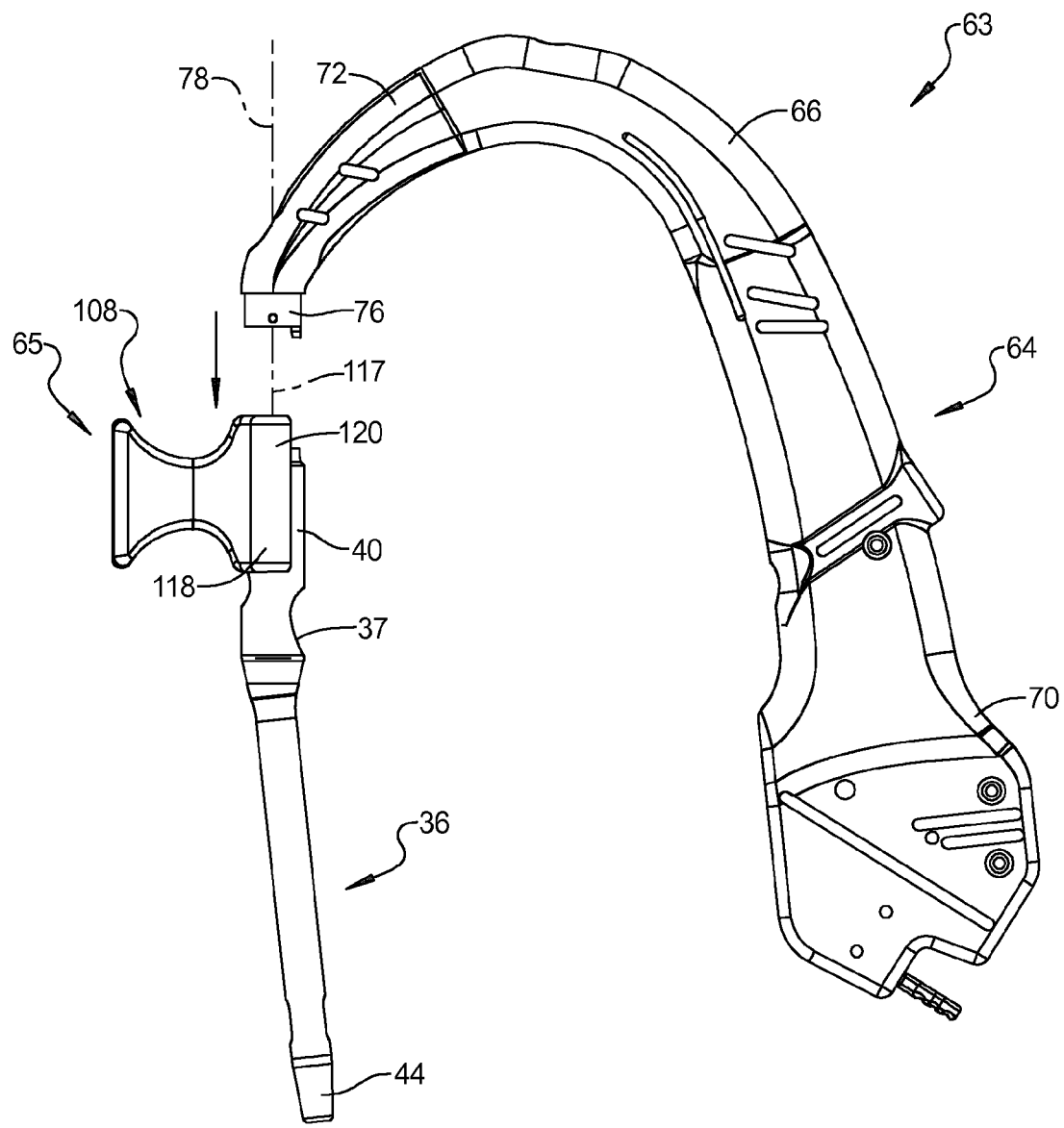
FIG. 13 is side plan view of the targeting instrument system of FIG. 2 with the detachable holding device coupled to the IM nail.

Turning now to the methods of the present teachings, FIGS. 12-14 illustrate one example of establishing a temporary locking alignment between a targeting guide device 64 and an intramedullary implant 36. For purposes of uniformity, FIGS. 12-14 use the detachable holding device 65 of FIG. 6; however, it should be understood that the other holding devices 126, 134 can also be used with the methods described herein. The methods generally begin by coupling the distal end 118 of the detachable holding device 65 to an intramedullary implant 36. With reference to FIG. 12, the detachable holding device 65 may be aligned with the proximal shaft 40 of the IM nail 36 such that the longitudinal axis 117 of the elongated receiving channel 116 is brought into line with the proximal shaft axis 42 of the IM nail 36. The holding device 65 can be moved in a direction normal to the longitudinal axis 117 until it abuts with the IM nail 36. Once adjacent to the IM nail 36, the holding device 65 can be further pressed against the IM nail 36 in order to outwardly flex the arms 114 to accommodate a snap-fit positioning of the distal end 118 of the elongated receiving channel 116 over the IM nail 36.

Next, with reference to FIG. 13, the proximal end 120 of the detachable holding device 65 is positioned adjacent the connection end 96 or shaft 76 of the nose component 72 of the targeting guide device 64. In one aspect, the longitudinal axis 117 is aligned with the nose component axis 78 and the targeting guide device 64 is slowly moved in a coaxial direction along the longitudinal axis 117 of the elongated receiving channel 116. If one or more of the holding device 65, IM nail 36, and/or the connection end 96 of the targeting guide device 64 are provided with respective interlocking features, as discussed above and referenced in FIGS. 5 and 9, the interlocking features are aligned together commensurate with the final axial movement and coupling of the connection end 96 with the receiving channel 116 and IM nail 36.

Alternatively, the connection end 96 of the targeting guide device 64 may be aligned with the IM nail 36 first, and the respective arms of the holding device 65, 126 may subsequently be snap-fit positioned over both the connection end 96 and the IM nail 36 at the same time. With regard to aspects incorporating the detachable holding device 134 of FIGS. 11A and 11B, users can use two fingers to press the ends 146, 146A, 146B of the grip portion 108 together to overcome the biasing force and separating the two clamp bodies 136, 138, which can then be positioned to grippingly engage both the connection end 96 and the IM nail 36 at the same time (FIG. 11A) or independently (FIG. 11B).

With reference to FIG. 14, once the detachable holding device 65 is coupled to both the IM nail 36 and the targeting guide device 64, thereby providing a temporary locking alignment, a user's hands may then be free to insert a connecting bolt 148. The connecting bolt 148 is configured to firmly connect the targeting guide device 64 to the IM nail 36 prior to the various additional steps typically involved with implanting the IM nail 36. The connecting bolt 148 is first aligned with the nose component axis 78 and moved through a portion of the targeting guide device 64, such as the nose shaft 76. Once it passes the nose shaft 76, the connecting bolt 148 is threadably fastened to a bore defined in the IM nail 36.

The detachable holding device 65 is then removed after the connecting bolt 148 is fastened.

The foregoing discussion discloses and describes merely exemplary arrangements of the present teachings. The embodiments described herein are not intended to be limiting in describing the full scope of implant devices and methods of the present technology. Equivalent changes, modifications and variations of embodiments, materials, components, and methods can be made within the scope of the present technology, with substantially similar results. Furthermore, the mixing and matching of features, elements, and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings.

What is claimed is:

1. A detachable holding device for the temporary locking connection of an intramedullary implant to a targeting guide device, the detachable holding device comprising:
    an exterior grip portion; and
    a clamp portion defining an interior engaging surface for coupling and maintaining a locking alignment between the intramedullary implant and the targeting guide device during the placement of the intramedullary implant into a subject, the clamp portion including two pivotally coupled clamp bodies joined by a shaft rod, the clamp bodies biased toward one another and having contoured arms configured to define a variably shaped elongated receiving channel commensurate with a diameter or shape of the intramedullary implant, the elongated receiving channel configured to grippingly engage the targeting guide device and the intramedullary implant.

2. The detachable holding device according to claim 1, wherein the elongated receiving channel extends from a proximal end configured to releasably engage the targeting guide device and a distal end configured to releasably engage the intramedullary implant.

3. The detachable holding device according to claim 1, comprising an injection molded plastic wherein a cross-section of the interior engaging surface of the clamp portion is substantially C-shaped defining the elongated receiving channel.

4. The detachable holding device according to claim 1, wherein the elongated receiving channel includes a longitudinal axis and the exterior grip portion extends a distance substantially perpendicular to the longitudinal axis.

5. The detachable holding device according to claim 1, wherein the clamp portion comprises at least one interlocking feature preventing rotation of intramedullary implant relative to the targeting guide device.

6. A targeting instrument system for positioning an intramedullary implant, the system comprising:
    a targeting guide device;
    an intramedullary implant;
    a connecting bolt; and
    a detachable holding device including an exterior grip portion and a clamp portion defining an interior engaging surface, the clamp portion maintaining a locking alignment between the intramedullary implant and the targeting guide device during the placement of the connecting bolt into the targeting guide device and the intramedullary implant.

7. The targeting instrument system of claim 6, wherein the targeting guide device comprises a generally U-shaped body and includes a handle portion and a nose portion, the nose portion defining a connection end configured for coupling to the intramedullary implant.

8. The targeting instrument system of claim 7, wherein the clamp portion and at least one or both of the intramedullary implant and the connection end of the nose portion comprise respective interlocking features preventing rotation of the intramedullary implant with respect to the targeting guide device.

9. The targeting instrument system of claim 6, wherein the clamp portion of the detachable holding device defines an elongated receiving channel having a proximal end configured to releasably engage the targeting guide device and a distal end configured to releasably engage the intramedullary implant.

10. The targeting instrument system of claim 9, wherein the detachable holding device comprises an injection molded plastic and the clamp portion has a substantially C-shaped cross-section extending from the proximal end to the distal end.

11. The targeting instrument system of claim 6, wherein the clamp portion comprises at least two flexible, spaced apart arms defining an elongated receiving channel.

12. The targeting instrument system of claim 6, wherein the detachable holding device comprises a polymeric material having a degree of flexibility sufficient to grippingly engage the targeting guide device and the intramedullary implant in a locking connection.

13. The targeting instrument system of claim 6, wherein the detachable holding device comprises two pivotally coupled clamp bodies, the clamp bodies biased toward one another and defining a contoured interior engaging surface configured to grippingly engage the targeting guide device and the intramedullary implant.

14. A method for establishing a temporary locking alignment between a targeting guide device and an intramedullary implant, the method comprising:

coupling a proximal end of a detachable holding device to a connection end of the targeting guide device;

coupling a distal end of the detachable holding device to an intramedullary implant;

inserting a connecting bolt through a portion of the targeting guide device and fastening the connecting bolt to the intramedullary implant; and removing the detachable holding device.

15. The method according to claim 14, wherein the detachable holding device comprises at least two flexible arms defining an elongated receiving channel, and at least one of the steps of coupling the proximal and distal ends of the detachable holding device comprises a snap-fit positioning of the respective intramedullary implant and the connection end of the targeting guide device between the flexible arms and into the elongated receiving channel.

16. The method according to claim 15, wherein the detachable holding device is moved in a direction normal to a longitudinal axis of the elongated receiving channel to accommodate the snap-fit positioning of the intramedullary implant into the elongated receiving channel and the connection end of the targeting guide device is moved in an axial direction along the longitudinal axis, entering the elongated channel from the distal end for alignment with the intramedullary implant.

17. The method according to claim 14, wherein the detachable holding device comprises two pivotally coupled biased clamp bodies, and the steps of coupling the proximal and distal ends of the detachable holding device to the targeting guide device and the intramedullary implant comprise separating the clamp bodies and positioning the detachable holding device to grippingly engage a connection end of the targeting guide device and the intramedullary implant.

18. The method according to claim 14, wherein the detachable holding device and at least one of the intramedullary implant and the connection end of the targeting guide device comprise respective interlocking features, and at least one of the respective steps of coupling the proximal and distal ends of the detachable holding device to the targeting guide device and the intramedullary implant further comprises aligning the interlocking features.

\* \* \* \* \*